(12) United States Patent
Stokes

(10) Patent No.: US 6,493,591 B1
(45) Date of Patent: Dec. 10, 2002

(54) IMPLANTABLE ACTIVE FIXATION LEAD WITH GUIDEWIRE TIP

(75) Inventor: Kenneth Blaine Stokes, Anoka, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/619,201

(22) Filed: Jul. 19, 2000

(51) Int. Cl.[7] ................................. A61N 1/00
(52) U.S. Cl. ........................................ 607/127
(58) Field of Search .................. 607/115, 116, 607/122–132; 600/585, 375

(56) References Cited

U.S. PATENT DOCUMENTS

| | | | |
|---|---|---|---|
| 3,769,984 A | 11/1973 | Muench | 128/404 |
| 4,057,067 A | 11/1977 | Lajos | 128/418 |
| 4,454,888 A | 6/1984 | Gold | 128/785 |
| 4,488,561 A | 12/1984 | Doring | 128/786 |
| 4,815,478 A | 3/1989 | Buchbinder et al. | 128/772 |
| 4,884,567 A | * 12/1989 | Elliott et al. | |
| 4,957,110 A | * 9/1990 | Vogel et al. | |
| 5,120,308 A | * 6/1992 | Hess | |
| 5,224,491 A | 7/1993 | Mehra | 128/784 |
| 5,304,218 A | * 4/1994 | Alferness | |
| 5,313,967 A | 5/1994 | Lieber et al. | 128/772 |
| 5,431,649 A | * 7/1995 | Mulier et al. | |
| 5,531,780 A | * 7/1996 | Vachon | |
| 5,571,163 A | * 11/1996 | Helland | |
| 5,596,996 A | 1/1997 | Johanson et al. | 128/772 |
| 5,916,178 A | 6/1999 | Noone et al. | 600/585 |
| 5,935,160 A | 8/1999 | Auricchio et al. | 607/122 |
| 5,991,668 A | 11/1999 | Leinders et al. | 607/125 |
| 6,006,122 A | 12/1999 | Smits | 600/373 |
| 6,033,414 A | 3/2000 | Tockman et al. | 606/129 |
| 6,042,876 A | 3/2000 | Deem | 427/2.28 |
| 6,321,102 B1 | * 11/2001 | Sephr et al. | |

FOREIGN PATENT DOCUMENTS

WO WO 93/04722 * 3/1993

* cited by examiner

Primary Examiner—Mark Bockelman
(74) Attorney, Agent, or Firm—Girma Wolde-Michael

(57) ABSTRACT

A lead adapted to be located within the cardiac vasculature is disclosed. The lead may be readily steered to a desired location within the cardiac vasculature to thereafter be securely located at a desired pacing site. The lead is provided with an improved electrode assembly located at its distal tip. The electrode assembly includes a fixation helix and a guidewire-like projection, both extending from the distal end of the lead body. The fixation helix, which may serve as all or part of the active electrode surrounds a structure corresponding to the distal end of a conventional guidewire. The fixation helix is mounted around the guidewire tip so that the sharpened tip of the helix lies closely adjacent to the guidewire tip, in a region of the guidewire tip which is sufficiently flexible to allow it to be moved away from the sharpened tip of the helix. The guidewire tip, which may be provided with a preformed curve at its distal end, is employed to navigate the lead through the cardiac vasculature in a fashion similar to the navigation of a catheter and guidewire in combination or a guidewire alone. Upon reaching the desired location within the cardiac vasculature, the lead may be rotated to screw one or more turns of the fixation helix into heart tissue, the flexibility of the guidewire tip allowing it to move away from the sharpened tip of the helix during the process of affixing the lead to the tissue.

18 Claims, 2 Drawing Sheets

IMPLANTABLE ACTIVE FIXATION LEAD WITH GUIDEWIRE TIP

BACKGROUND OF THE INVENTION

The present invention relates to implantable electrode leads generally, and more particularly to leads adapted for use in the coronary sinus.

Recently, an increased interest in pacing the left atrium and ventricle of the heart has led to a resurgence of interest in location of cardiac pacing leads in the coronary sinus, great vein, or other cardiac vein. To this end, the use of guidewire placed leads, as disclosed in U.S. Pat. No. 3,769,984 issued to Muench, has resurfaced, leading to the development of a number of coronary sinus pacing leads intended to be advanced into a desired location within the cardiac vasculature over a guidewire. Some examples of such leads are disclosed in U.S. Pat. No. 6,033,414 issued to Tockman et al., U.S. Pat. No. 5,935,160 issued to Auricchio et al., and U.S. Pat. No. 5,304,218 issued to Alferness. As an alternative to advancing a lead to a desired position by means of a guidewire, it has also been proposed to fashion the tip of a lead with a preformed curve, so that the tip of the lead itself may be used to steer the lead through the cardiac vasculature. Such a lead is disclosed in U.S. Pat. No. 6,006,122 issued to Smits. In addition to renewed interest in locating leads within the cardiac veins, there has been significant developmental effort expended on solving the problem of maintaining a lead in a desired location in the cardiac veins. One group of solutions to this problem has been to provide the lead with a preformed set of bends or curves in the lead body, temporarily straightened by stylet, which upon removal of the stylet expand to wedge the lead within the cardiac veins. Examples of leads of this type are disclosed in U.S. Pat. No. 4,488,561 issued to Doring, U.S. Pat. No. 4,454,888 issued to Gold and U.S. Pat. No. 4,057,067 issued to Lajos, An alternative set of mechanisms for location of leads has been to provide an electrode, which is either configured to be wedged in the cardiac veins, or which is adapted to be expanded into contact with the wall of the cardiac veins. Such electrodes are disclosed in U.S. Pat. No. 6,006,122 issued to Smits, U.S. Pat. No. 5,224,491 issued to Mehra, and U.S. Pat. No. 5,991,668 issued to Leinders.

SUMMARY OF THE INVENTION

The present invention is directed toward a lead adapted to be located within the cardiac vasculature, which may be readily steered to a desired location within the cardiac vasculature and thereafter securely located at a desired pacing site. The present invention accomplishes these desired results by means of a lead provided with an improved electrode assembly located at its distal tip. The electrode assembly includes a fixation helix and a guidewire-like projection, both extending from the distal end of the lead body. The fixation helix, which may serve as all or part of the active electrode surrounds a structure corresponding to the distal end of a conventional guidewire (hereafter referred to as the "guidewire tip"). The fixation helix is mounted around the guidewire tip in such a fashion that the sharpened tip of the helix lies closely adjacent to the guidewire tip, in a region of the guidewire tip which is sufficiently flexible to allow it to be moved away from the sharpened tip of the helix. The guidewire tip, which may be provided with a preformed curve at its distal end, is employed to navigate the lead through the cardiac vasculature in a fashion similar to the navigation of a catheter and guidewire in combination or a guidewire alone. Upon reaching the desired location within the cardiac vasculature, the lead may be rotated to screw one or more turns of the fixation helix into heart or blood vessel tissue, the flexibility of the guidewire tip allowing it to move away from the sharpened tip of the helix during the process of affixing the lead to the tissue.

DETAILED DESCRIPTION OF THE PREFERRED EMBODIMENT

Figure 1:
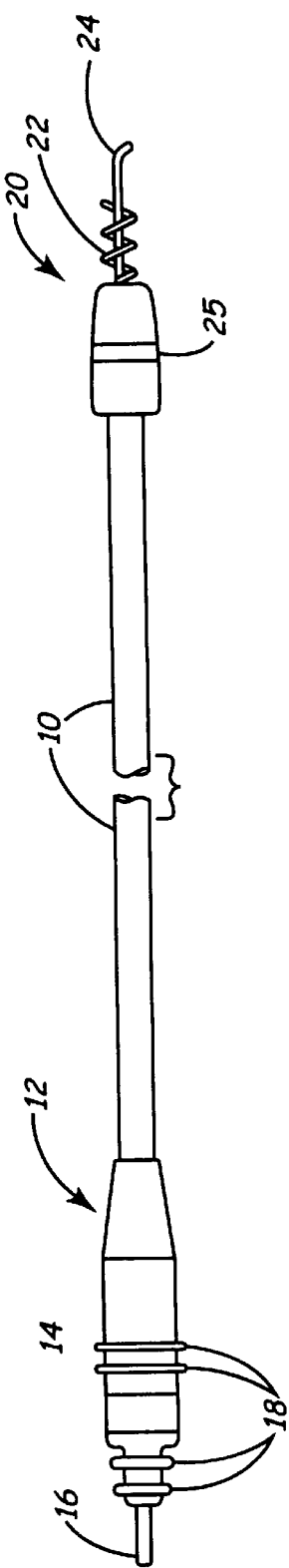
FIG. 1 is a plan view of a lead according to the present invention.

FIG. 1 is a plan view of a lead according to the present invention. The lead is provided with an elongated insulative lead body that carries one or more conductors extending along its length. At the proximal end of the lead body is a connector assembly 12, which includes a connector pin 16 and a connector ring 14. In unipolar leads, connector pin 16 is conducted to a single conductor within lead body 10. In bipolar embodiments, connector ring 14 is coupled to a second conductor within lead body 10. Sealing rings 18 prevent ingress of fluids into the connector block of a pacemaker in which the lead is inserted and prevent flow of fluid between connector pin 16 and connector ring 14, in a conventional fashion.

At the distal end of the lead body is an electrode head assembly 20, from which a fixation helix 22 and a guidewire tip 24 protrude distally. The structure of the fixation helix 22 and the guidewire tip 24 are discussed in more detail in conjunction with FIGS. 2 and 3 below. In the embodiment illustrated, helix 22 serves as an electrode, coupled via a conductor to connector pin 16. The helix 22 may be electrically insulated from guidewire tip 24, or alternatively, the guidewire tip 24 may be used in conjunction with helix 22 as the electrode. In bipolar embodiments, a separate electrode surface such as ring 25 might be provided at the distal end of lead body 10 that is coupled via a conductor to connector ring 14. When used in a bipolar configuration, the second electrode may be provided by the guidewire tip 24, which is insulated electrically from helix 22, as discussed below in reference to FIG. 4. Alternatively, the helix 22 may be used in conjunction with guidewire tip 24 as the second electrode.

Figure 2:
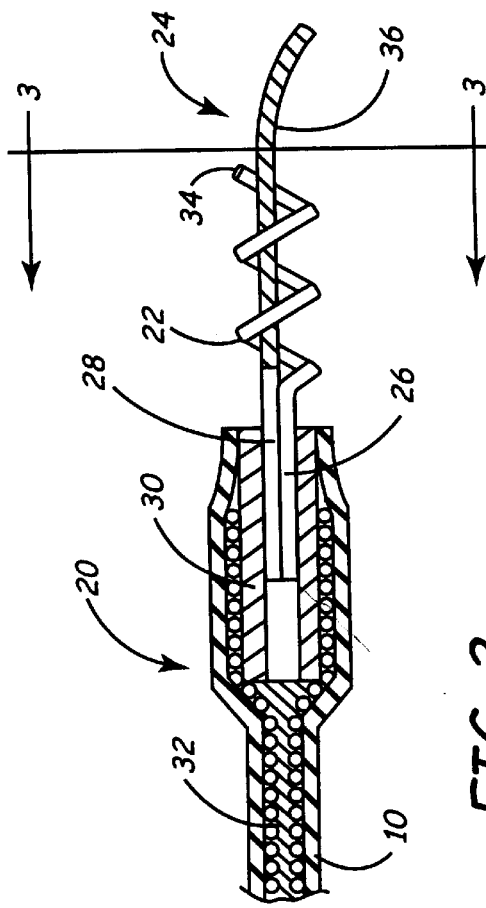
FIG. 2 is a cutaway view through the distal portion of the lead of FIG. 1.

FIG. 2 is a cutaway view through the distal portion of the lead of FIG. 1. In this view, the internal and external structures of the electrode head assembly 20 are revealed in more detail. The lead body 10 is seen to take the form of an elongated insulative sheath of biocompatible plastic such as polyurethane or silicone rubber. Located within the sheath is an elongated conductor 32, which in the embodiment illustrated takes the form of a coiled conductor. Stranded or cabled conductors may, be substituted. As illustrated, a guidewire tip 24 and a fixation helix 22 are shown having their proximal portions 28 and 26, respectively, crimped together within a tubular metallic sleeve 30. Conductor 32 is coupled electrically and mechanically to sleeve 30 by crimping, welding, or other conventional mechanism.

As illustrated, guidewire tip 24 corresponds to the tip portion of a conventional guidewire of the type typically employed in conjunction with angioplasty or diagnostic catheters. The proximal portion 28 of the guidewire tip 24 may take the form of a length of hypodermic tubing, with the more flexible distal portion 36 of the guidewire tip taking the form of an elongated coil. A core member typically will extend from the distal end of hypodermic tubing 28 through the coil 36 and may or may not be coupled to the distal tip of the coil 36. Guidewire tip structures which may be employed in the context of the present invention are illustrated, for example, in U.S. Pat. No. 6,042,876 issued to Deem, U.S. Pat. No. 4,815,478 issued to Buchbinder, and U.S. Pat. No. 5,596,996 issued to Johanson et al., incorporated herein by reference in their entireties. Alternatively, the guidewire tip 24 may be a unitary guidewire tip of the type sometimes employed in conjunction with nitinol guidewires, for example, as disclosed in U.S. Pat. No. 5,916,178 issued to Noone et al. or U.S. Pat. No. 5,313,967 issued to Lieber et al., also incorporated herein by reference in their entireties.

Fixation helix 22 comprises a helical portion and a proximally extending shank portion 26, crimped within sleeve 30. At the distal end of helix 22 is a sharpened, chiseled point, facilitating entry of the fixation helix into heart or blood vessel tissue. As illustrated, the helix is mounted so that the guidewire tip 24 extends eccentrically through the helix, such that chisel tip 34 of the helix lies closely adjacent the more flexible distal portion 36 of guidewire tip 24. The location of chisel tip 34 in close proximity to the distal portion 36 of guidewire tip 24 prevents vascular damage prior to fixation since chisel tip is less likely to inadvertently become embedded in tissue as the lead is navigated through the vasculature. In use, as fixation helix 22 is rotated to embed chisel tip 34 in heart or blood vessel tissue, the flexibility of guidewire tip 24 allows it to move away from helix 22, facilitating further rotation of the helix into the tissue and providing stabilization of the lead at its desired location.

Figure 3:
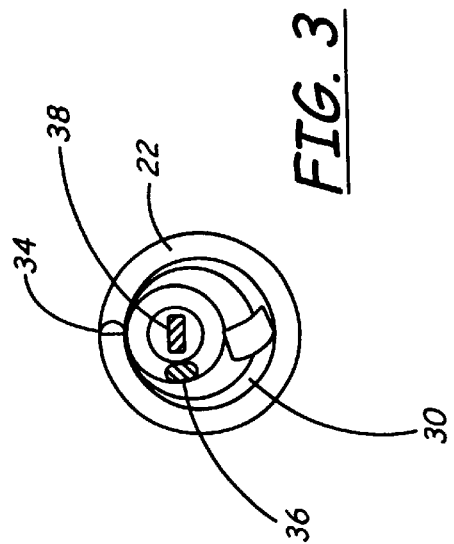
FIG. 3 is a cross-sectional view through the distal tip of the lead, taken through the flexible portion of the guidewire tip.

FIG. 3 is a cross-sectional view through the lead of FIG. 1 taken at a point slightly distal to the chisel tip 34 of fixation helix 22. In this view, it can be seen that the distal portion 36 of guidewire tip 24 is in fact a fine coil with a flattened core wire 38 extending therethrough. In an alternative embodiment, the core wire is generally tubular. The distal surface of sleeve 30, crimped around guidewire tip 24 and helix 22 is also visible in this view. FIG. 3 also illustrates the arrangement by which the sharpened chisel tip 34 of the helix lies closely adjacent to the distal portion 36 of the guidewire tip.

Figure 4:
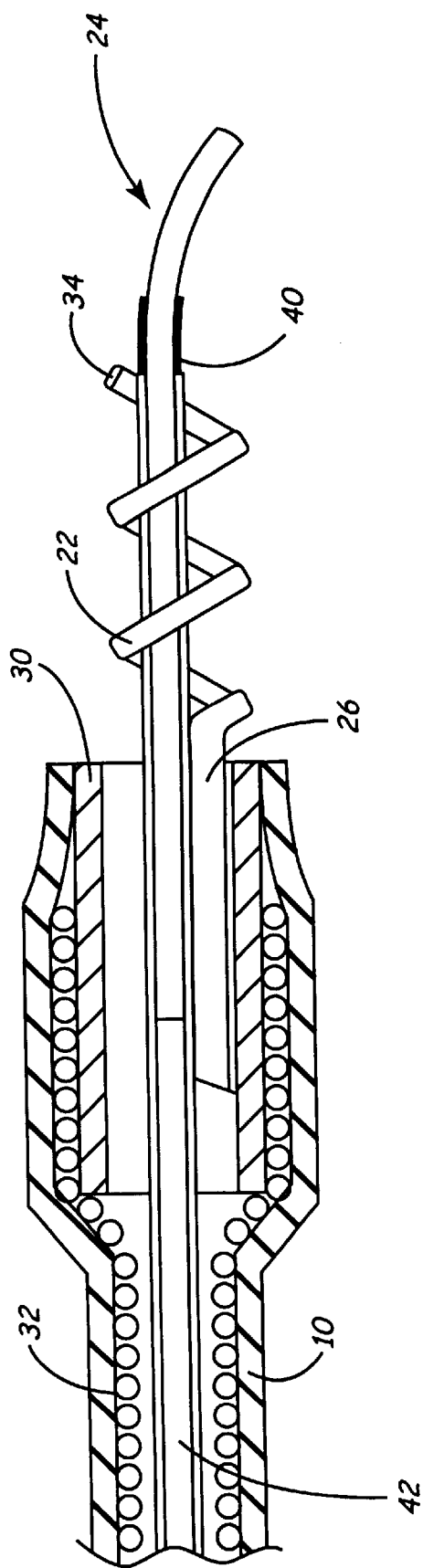
FIG. 4 is a cutaway view through the distal portion of the lead of FIG. 1 showing an alternative embodiment wherein the guidewire tip is insulated from the helix.

FIG. 4 is a cutaway view through the distal portion of the lead of FIG. 1 showing an alternative embodiment wherein the guidewire tip is insulated from the helix. This view shows the various aspects of the lead of FIG. 2, and further include insulative sheath 40 electrically insulating guidewire tip 24 from helix 22. In a bipolar arrangement, helix 22 may be utilized as a first electrode electrically coupled to either connector pin 16 or connector ring 14 via a respective conductor. Guidewire tip 24 serves as the second electrode electrically coupled to the other connector via a conductor shown as conductor 42 of FIG. 4. In one embodiment, a bipolar configuration having a 2.9 French diameter may be implemented using an insulative coating 40 of biostable polyimide such as GENYMERE™ polyimide or other appropriate insulating material on each wire of the conductor coil. In one embodiment, the coating is 0.0002 to 0.001 inches thick.

The above-illustrated embodiment is exemplary of one type of lead in which the present invention may be practiced. However, the present invention may also be usefully practiced in leads having additional electrodes, sensors, alternative connector assemblies, and the like. The basic construction of the improved electrode head assembly of the present invention is believed useful in conjunction with lead bodies and connectors of any of the various known varieties. As such, the embodiment described above should be considered as exemplary rather than limiting with regard to the claims that follow.

In conjunction with the above specification, I claim:

1. A medical electrical lead comprising:

an elongated lead body carrying an electrical conductor therein and an electrode head assembly, located at a distal end of the lead body, wherein the electrode head assembly comprises a distally extending fixation helix having a distal tip and a flexible guidewire tip extending through the fixation helix and arranged such that the tip of the fixation helix is located closely adjacent the flexible guidewire tip wherein said guidewire is fixed to said electrode assembly head preventing longitudinal movement within the assembly and wherein said guidewire is sufficiently flexible to move away from said helix to permit tissue insertion.

2. A lead according to claim 1 wherein the flexible guidewire tip comprises a proximal, relatively stiffer portion which is fixedly mounted to the lead and a distally extending, more flexible portion, and wherein the tip of the fixation helix lies adjacent the distally extending, more flexible portion of the guidewire tip.

3. A lead according to claim 1 or claim 2 wherein the distal tip of the fixation helix is a sharpened tip.

4. A lead according to claim 1 or claim 2 wherein the guidewire tip is a unitary core structure.

5. A lead according to claim 1 or claim 2 wherein the lead body further carries at least one biological sensor.

6. A lead according to claim 1 or claim 2 wherein a distal portion of the flexible guidewire tip is a coil having a core wire extending therethrough.

7. A lead according to claim 6 wherein a proximal portion of the flexible guidewire tip is hypodermic tubing.

8. A lead according to claim 1 or 2, wherein the electrical conductor is coupled to the fixation helix, and wherein the fixation helix serves as a first electrode.

9. A lead according to claim 8, wherein the electrical conductor is further electrically coupled to the flexible guidewire tip.

10. A lead according to claim 8, and further including an insulative sheath electrically insulating the flexible guidewire tip from the fixation helix.

11. A lead according to claim 10, wherein the insulative sheath is biostable polyimide.

12. A lead according to claim 11, wherein the insulative sheath is GENYMERE™ polyimide.

13. A lead according to claim 10, and further including a second electrical conductor coupled to the flexible guidewire tip, wherein the flexible guidewire tip serves as a second electrode.

14. A lead according to claim 8, wherein the lead body includes a second ring electrode and the lead body further carries a second conductor coupled to the second ring electrode.

15. A lead according to claim 1 or claim 2, wherein the electrical conductor is coupled to the flexible guidewire tip, and wherein the flexible guidewire tip serves as a first electrode.

16. A lead according to claim 13, and further including an insulative sheath electrically insulating the flexible guidewire tip from the fixation helix.

17. A lead according to claim 14, wherein the insulative sheath is Genymere polyimide.

18. A lead according to claim 14, wherein the lead body includes a second ring electrode and the lead body further carries a second conductor coupled to the second ring electrode.

* * * * *

UNITED STATES PATENT AND TRADEMARK OFFICE
Certificate

Patent No. 6,493,591 B1                                                              Patented: December 10, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Kenneth Blaine Stokes, Anoka, MN (US); Michael J. Ebert, Fridley, MN (US); and Kenneth R. Brennen, Zimmerman, MN (US).

Signed and Sealed this First Day of March 2011.

CARL H. LAYNO
*Supervisory Patent Examiner*
Art Unit 3766
Technology Center 3700